United States Patent [19]

Merianos

[11] Patent Number: 5,352,833
[45] Date of Patent: * Oct. 4, 1994

[54] ANTIBACTERIAL POLYMERIC QUATERNARY AMMONIUM COMPOUNDS

[75] Inventor: John J. Merianos, Middletown, N.J.

[73] Assignee: ISP Investments Inc., Wilmington, Del.

[*] Notice: The portion of the term of this patent subsequent to Sep. 7, 2010 has been disclaimed.

[21] Appl. No.: 966,496

[22] Filed: Oct. 26, 1992

[51] Int. Cl.$^5$ .................... C07C 217/42; A61K 31/14
[52] U.S. Cl. .................... 564/294; 564/292; 564/295
[58] Field of Search ............... 514/642, 839, 840, 422; 564/294, 295, 292; 424/78.04; 422/28; 523/122; 548/543

[56] References Cited

U.S. PATENT DOCUMENTS

| | | | |
|---|---|---|---|
| 3,898,336 | 8/1975 | Rembaum et al. | 514/642 |
| 3,931,319 | 1/1976 | Green et al. | 564/295 |
| 4,778,813 | 10/1988 | Fenyes et al. | 514/642 |
| 4,978,685 | 12/1990 | Gannon et al. | 514/642 |
| 5,145,643 | 9/1992 | Dziabo et al. | 422/28 |
| 5,242,684 | 9/1993 | Merianos, Jr. | 564/294 |

*Primary Examiner*—Peter O'Sullivan
*Attorney, Agent, or Firm*—Marilyn J. Maue; Walter Katz; Joshua J. Ward

[57] ABSTRACT

What is provided herein are active antimicrobial polymeric quaternary ammonium compounds which are capped with defined $C_{12}/C_{14}$ alkyl groups optionally coprecipitated with polyvinylpyrrolidone (PVP). The compounds of the invention have the formula:

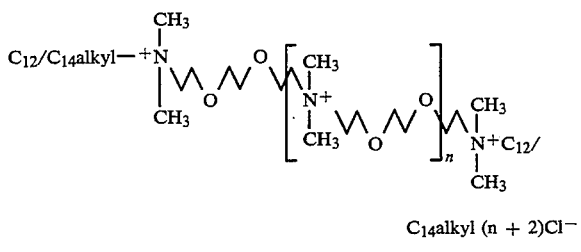

where n is at least 2, e.g. 2-30, and $C_{12}/C_{14}$ alkyl preferably is 50:50 wt. % of dodecyl/tetradecyl alkyl.

4 Claims, No Drawings

ANTIBACTERIAL POLYMERIC QUATERNARY AMMONIUM COMPOUNDS

BACKGROUND OF THE INVENTION

1. Field of the Invention

This invention relates to polymeric quaternary ammonium compounds, and, more particularly, to antimicrobial polymeric quaternary ammonium compounds capped with $C_{12}/C_{14}$ alkyldimethyl groups, optionally coprecipitated with polyvinylpyrrolidone.

2. Description of the Prior Art

Green et al, in U.S. Pat. No. 3,931,319, described microbiocidal quaternary ammonium polymers made by a two-step process comprising (a) condensing a difunctional tertiary amine with an excess of 1,4-dihalo-2-butene, and (b) capping the reaction product with a calculated amount of a monofunctional tertiary amine. The product was a linear polymer whose termini at both ends were quaternary ammonium moieties. This polymer has achieved commercial success as a disinfectant for contact lens solutions (for example, Softlens, Millmaster Onyx Corp.).

Green et al, in U.S. Pat. No. 4,027,020, described the preparation of the same capped polymers as in U.S. Pat. No. 3,931,319 by the direct, one-step reaction between a mixture of 1,4-dihalo-2-butene, a difunctional tertiary amine and a monofunctional tertiary amine. The polymer product was characterized as having chain lengths which varied from very short to very long, and molecular weights which varied from low to high over a comparatively wide range, in contrast to the two-step polymer which had high molecular weights and varied over a comparatively narrow range.

Accordingly, it is an object of this invention to provide improved antibacterial polymeric quaternary ammonium compounds which exhibits broad spectrum microbiological activity at a minimum, biological concentration and a lower toxicity which may cause hydrolysis of the polymeric compound.

Another object of this invention is to provide such improved compounds by both a one or a two-step process.

SUMMARY OF THE INVENTION

What is provided herein are an active antimicrobial polymeric quaternary ammonium compounds capped with a defined tertiary amine, optionally coprecipitated with polyvinylpyrrolidone (PVP), having the formula:

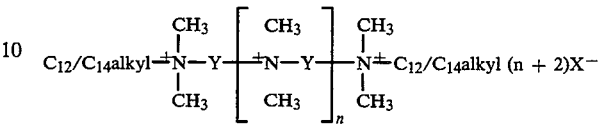

where
Y is alkylene interrupted with oxygen,
X is a halogen selected from Cl and Br, and
n is 2–30.

A preferred compound is:

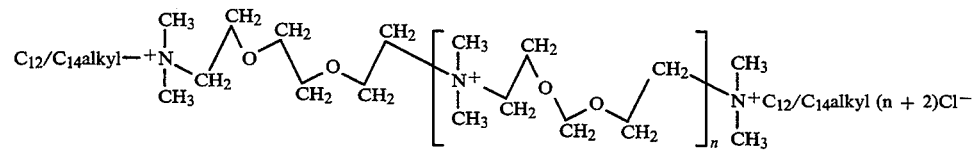

where n is at least 2, e.g. 2–30, and $C_{12}/C_{14}$ is a dodecyl/tetradecyl alkyl, e.g. a 50:50 wt. % mixture. This compound can be made by reaction of 1,2-bis(dimethylaminoethoxide) ethane or dimethylamine with a slight excess of triethylene glycol dichloride, followed by end-capping of the chloro-terminated polymeric quat with a small amount of dodecyl/tetradecyl dimethylamine (e.g. a 50:50 wt. % mixture); and optionally including coprecipitation of the reaction product with PVP.

The product of the invention requires only a minimum inhibitory concentration (MIC) of 5–20 ppm against representative microorganisms, and exhibits reduced toxicity, as compared to the Green compounds.

DETAILED DESCRIPTION OF THE INVENTION

The antimicrobial polymeric quaternary ammonium (quat) products of the invention may be prepared by reaction of a 1,2-bis(dimethylaminoethoxide) ethane (DBE) with a slight molar excess of triethylene glycol dichloride, in a 50:50 water-methanol solvent, under reflux, for about 18 hours, followed by end-capping of any unreacted chloro-terminated groups in the polymer with a mixture of 50% dodecyl/50% tetradecyldimethylamine (c).

Reaction A

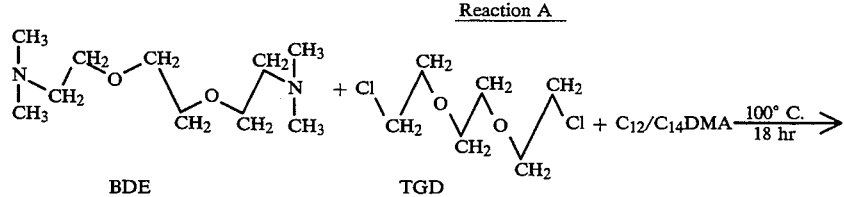

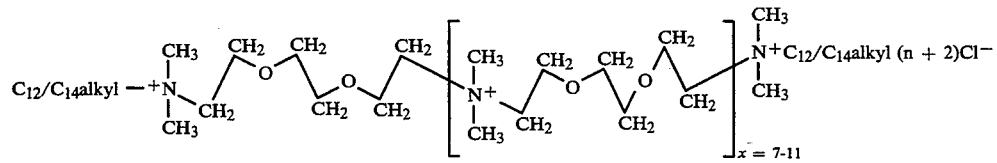

Alternatively, the difunctional amine BDE may be replaced by a dimethylamine and sodium hydroxide as illustrated in Example 2, with similar results except that the x value in the reaction product is about 5–9.

EXAMPLE 1

| Reactants | MW | Amt. (g) | Moles |
|---|---|---|---|
| 1,2-Bis(dimethylaminoethoxyl) ethane (BDE) | 204 | 36.7 | 0.18 |
| Triethyleneglycol dichloride (TGD) | 187 | 37.4 | 0.2 |
| Dodecyl/tetradecyl (50:50) dimethylamine ($C_{12}/C_{14}$ DMA) | 227 | 9.1 | 0.04 |

The BDE and TGD reactants were dissolved in 200 g of water-methanol (50:50) solvent and heated at reflux for 18 hours. The progress of the reaction was monitored by GC analysis of samples taken periodically for disappearance of the starting materials. Then the $C_{12}/C_{14}$ DMA reactant was added and heating at reflux was continued for another 6 hours. Samples were analyzed for disappearance of TGD and $C_{12}/C_{14}$ DMA reactants. The reaction product was evaporated under vacuum, and the residue was-washed with acetone and dried to provide 67.8 g. of an amorphous precipitate (x=7−11). Yield 81.5%.

The precipitate was dissolved in ethanol and coprecipitated with an equal amount of PVP-$C_1$ to give a 50% active product which was tested for antimicrobial activity against bacteria and fungi. The minimum inhibitory concentration (MIC) was 5–20 ppm and the minimum bactericidal concentration (MBC) was 10–50 against the following microorganisms:

| Microorganism | MIC | MBC |
|---|---|---|
| *Eschrechia coli* | 5 | 10 |
| *Pseudomonas aeruginosa* | 20 | 10 |
| *Pseudomonas cepacia* | 10 | 10 |
| *Streptococcus pyogenes* | 5 | 20 |
| *Staphylococcus aureus* | 5 | 10 |
| *Candida albican* | 15 | 10 |
| *Asperigillus niger* | 10 | 50 |
| *Asperigillus fumigatus* | 10 | 50 |

EXAMPLE 2

| Reactants | MW | Amt. (g) | Moles |
|---|---|---|---|
| Dimethylamine (DMA) (40%) | 112.5 | 22.5 | 0.20 |
| TGD | 187 | 46.75 | 0.25 |
| $C_{12}/C_{14}$ DMA | 227 | 22.7 | 0.10 |
| NaOH solution (40%) | 100 | 20.0 | 0.20 |

DMA and TGD were dissolved in 150 g. of a 50:50 water-methanol solvent and 20 g. of a 40% NaOH solution was added (pH 8–9). The reaction mixture was heated at 85°–90° C. for 24 hours whereupon all the NaOH solution was consumed. Then $C_{12}/C_{14}$ DMA was added and the mixture was heated for another 6 hours. The reaction was 98.5% completed based on GC analysis of TGD used. The reaction mixture was evaporated under reduced pressure to give an oil which was redissolved in absolute methanol. The white precipitate of NaCl (10.5 g) was filtered off and the methanolic solution was evaporated to dryness and dried in a dessicator over P205. Yield 63.4 g, 81.5%. The product had a similar antimicrobial activity against bacteria and fungi as the PVP product of Example 1.

The antibacterial polymeric quaternary ammonium compounds of the invention exhibit broad spectrum microbiological activity at a minimum biological concentration, and at a lower toxicity than previous, related compounds of the prior art.

While the invention has been described with particular reference to certain embodiments thereof, it will be understood that changes and modifications may be made which are within the skill of the art. Accordingly, it is intended to be bound only by the following claims, in which:

What is claimed is:

1. Antimicrobial polymeric quaternary ammonium compounds having the formula:

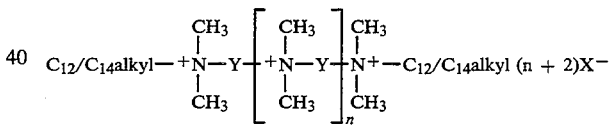

where Y is alkylene interrupted with oxygen,
X is selected from chlorine and bromine, and
n is 2–30.

2. Antimicrobial polymeric quaternary ammonium compounds according to claim 1 where $C_{12}/C_{14}$ alkyl is a 50:50 mixture of the alkyl groups.

3. Antimicrobial polymeric quaternary compounds according to claim 1 where X is chlorine.

4. Antimicrobial polymeric quaternary compounds according to claim 1 which have the formula

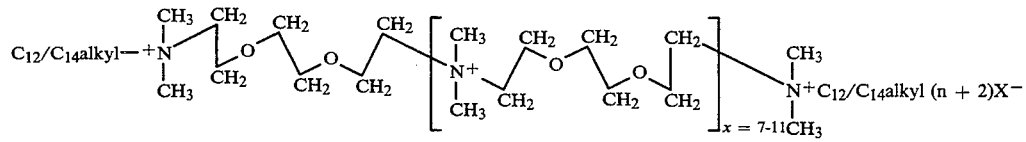

* * * * *